(12) United States Patent
Barry et al.

(10) Patent No.: US 7,694,810 B1
(45) Date of Patent: Apr. 13, 2010

(54) CARRIER TUBE ASSEMBLY FOR PACKAGING A MEDICAL DEVICE

(75) Inventors: Kevin Barry, Buffalo, MN (US); Robert N. Squire, Maple Grove, MN (US); Jeff Lindquist, Maple Grove, MN (US); Irina Nazarova, Woodbury, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

(21) Appl. No.: 12/393,943

(22) Filed: Feb. 26, 2009

(51) Int. Cl.
*B65D 85/20* (2006.01)

(52) U.S. Cl. .................. 206/364; 206/204; 206/438

(58) Field of Classification Search .............. 206/364, 206/363, 438, 204, 570; 604/192, 533, 171, 604/172, 263; 128/201.13, 204.17
See application file for complete search history.

(56) References Cited

U.S. PATENT DOCUMENTS

| | | | |
|---|---|---|---|
| 4,216,860 A | | 8/1980 | Heimann |
| 4,730,726 A | | 3/1988 | Holzworth |
| 5,217,114 A | * | 6/1993 | Gadberry et al. ............ 206/364 |
| 5,590,778 A | | 1/1997 | Dutchik |
| 5,848,691 A | | 12/1998 | Morris et al. |
| 5,874,045 A | * | 2/1999 | Chisum ...................... 422/58 |
| 5,935,501 A | | 8/1999 | Andrews et al. |
| 6,065,597 A | | 5/2000 | Pettersson et al. |
| 6,585,702 B1 | * | 7/2003 | Brunel ........................ 604/263 |
| 6,875,400 B2 | | 4/2005 | Speer et al. |
| 7,000,770 B2 | | 2/2006 | Clarke et al. |
| 7,108,682 B2 | | 9/2006 | Duffy et al. |
| 7,261,205 B2 | | 8/2007 | Cervantes |
| 2005/0109648 A1 | | 5/2005 | Kerzman et al. |
| 2005/0143803 A1 | | 6/2005 | Watson et al. |
| 2005/0199521 A1 | | 9/2005 | Givens, Jr. |
| 2005/0278012 A1 | * | 12/2005 | Vonderwalde .............. 623/1.11 |
| 2006/0086254 A1 | * | 4/2006 | Fudge et al. ................. 96/413 |
| 2006/0260967 A1 | | 11/2006 | Clarke et al. |

FOREIGN PATENT DOCUMENTS

| | | |
|---|---|---|
| EP | 0492399 | 7/1992 |
| EP | 0782868 | 7/1997 |

\* cited by examiner

*Primary Examiner*—Ehud Gartenberg
*Assistant Examiner*—King M Chu
(74) *Attorney, Agent, or Firm*—Crompton, Seager & Tufte, LLC

(57) ABSTRACT

A carrier tube assembly for packaging a medical catheter is disclosed. The carrier tube assembly includes an elongate tube, a medical catheter, and a plug. At least a distal portion of the elongate shaft of the medical catheter is positioned in the lumen of the elongate tube such that the proximal end of the elongate tube is hermetically sealed around a portion of the hub assembly of the medical catheter. The plug is inserted into the lumen of the elongate tube at the distal end of the elongate tube, hermetically sealing the distal end of the elongate tube. Thus, a hermetically sealed environment is established within the elongate tube. The plug includes a moisture and/or oxygen absorbing agent to absorb moisture and/or oxygen in the hermetically sealed environment.

26 Claims, 12 Drawing Sheets

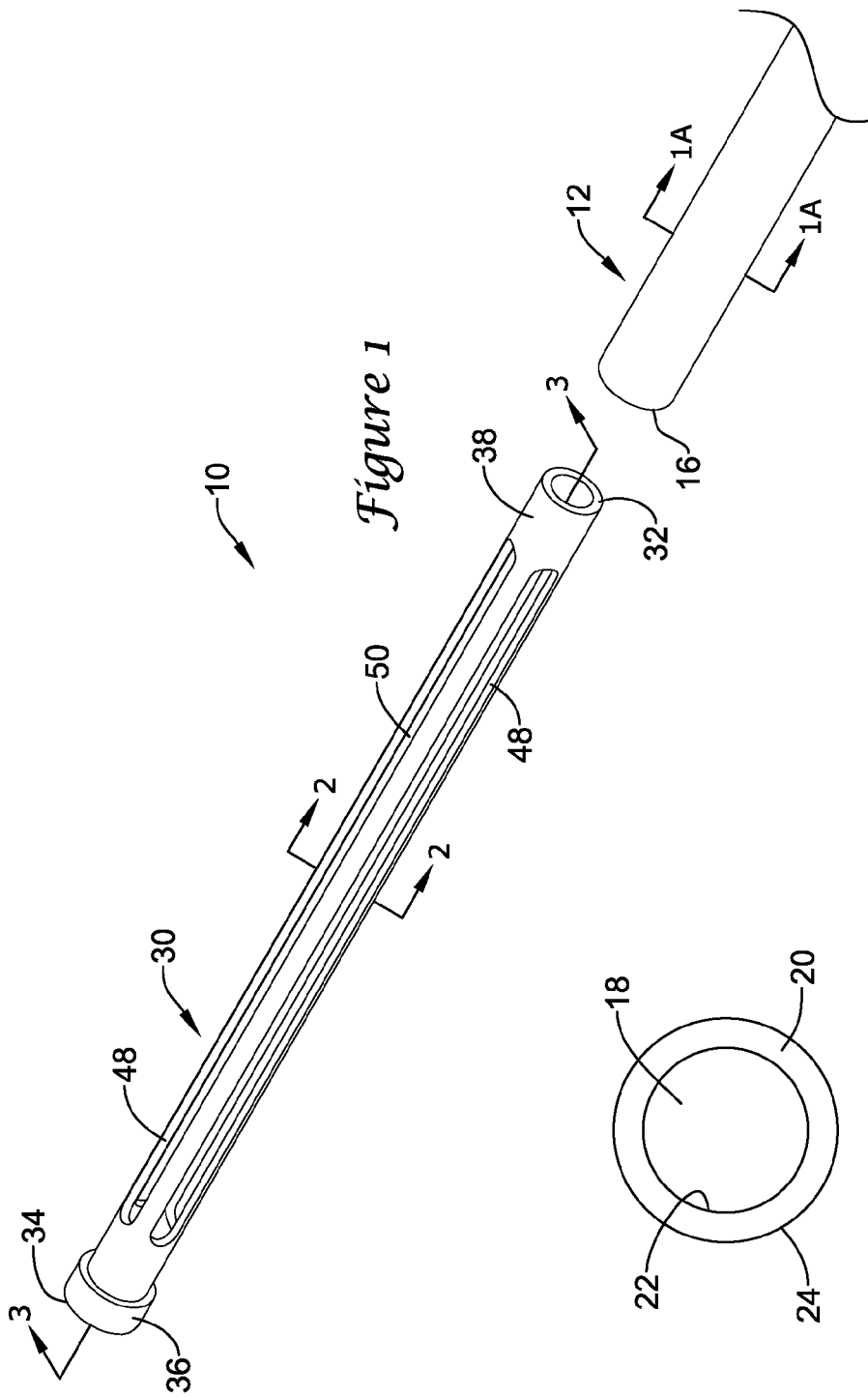

US 7,694,810 B1

CARRIER TUBE ASSEMBLY FOR PACKAGING A MEDICAL DEVICE

TECHNICAL FIELD

The disclosure is directed to a carrier tube assembly for packaging a medical device. More particularly, the disclosure is directed to a carrier tube hermetically sealed around a distal portion of a catheter and a plug hermetically sealing the distal end of the carrier tube. In some embodiments the carrier tube assembly includes means for reducing exposure of moisture and/or oxygen to the contents of the carrier tube.

BACKGROUND

Medical devices, such as catheters, are conventionally packaged in a sterilized package such as a pouch or a tray. Some medical devices include coatings, the integrity of which may be adversely affected by exposure to elevated levels of temperature, light, moisture, and/or oxygen. For example, levels of oxygen and/or moisture found in the sealed pouch or tray may negatively impact the functionality and/or performance of the coating.

There is a need to provide alternative packaging assemblies for providing a medical device, such as a catheter, in a sterilized environment and/or reducing the level of oxygen and/or moisture within the sealed environment surrounding the medical device.

SUMMARY

The disclosure is directed to several alternative designs, materials and methods of providing a sterilized environment for a medical device and/or reducing the level of oxygen and/or moisture within a sealed environment surrounding a medical device.

Accordingly, one illustrative embodiment is a carrier tube assembly for packaging a medical catheter. The carrier tube assembly includes an elongate tube, a medical catheter, and a plug. At least a distal portion of the elongate shaft of the medical catheter is positioned in the lumen of the elongate tube such that the proximal end of the elongate tube is hermetically sealed around a portion of the hub assembly of the medical catheter. The plug is inserted into the lumen of the elongate tube at the distal end of the elongate tube, hermetically sealing the distal end of the elongate tube. Thus, a hermetically sealed environment is established within the elongate tube. The plug includes a moisture and/or oxygen absorbing agent to absorb moisture and/or oxygen in the hermetically sealed environment.

Another illustrative embodiment is a carrier tube assembly for packaging a medical catheter. The carrier tube assembly includes an elongate tube, a medical catheter, and a plug. The medical catheter includes a hub assembly and an elongate shaft extending distally from the hub assembly. At least a distal portion of the elongate shaft of the medical catheter is positioned in the lumen of the elongate tube and the proximal end of the elongate tube is hermetically sealed around a portion of the hub assembly of the medical catheter. The plug is inserted into the lumen of the elongate tube at the distal end of the elongate tube. The plug hermetically seals the distal end of the elongate tube. Thus, a hermetically sealed environment is established within the elongate tube. The plug includes a means for reducing the quantity of moisture and/or oxygen within the hermetically sealed environment.

Another illustrative embodiment is a carrier tube assembly for packaging a medical catheter. The carrier tube assembly includes an elongate tube, a medical catheter, and a cylindrical plug. The medical catheter includes a hub assembly and an elongate shaft extending distally from the hub assembly. At least a distal portion of the elongate shaft of the medical catheter is positioned in the lumen of the elongate tube, wherein the proximal end of the elongate tube is hermetically sealed around a portion of the hub assembly of the medical catheter. The first end of the cylindrical plug is inserted into the lumen of the elongate tube at the distal end of the elongate tube such that the exterior surface of the plug is in contact with an inner surface of the elongate tube to hermetically seal the distal end of the elongate tube. The plug includes a central bore extending from the first end of the plug toward the second end of the plug, wherein the central bore defines an interior surface of the plug. The plug further includes one or more openings, such as elongate slots, extending into the central bore from the exterior surface to the interior surface. The central bore of the plug is in fluid communication with the lumen of the elongate tube. In some embodiments, the plug may include a moisture and/or oxygen absorbing agent to absorb moisture and/or oxygen sealed within the lumen of the elongate tube.

Yet another illustrative embodiment is a method of packaging and sterilizing a medical catheter. The method includes providing a medical catheter, an elongate tube, and a plug. At least a distal portion of the elongate shaft of the medical catheter is positioned into the lumen of the elongate tube and the proximal end of the elongate tube is hermetically sealed around a portion of the hub assembly of the medical catheter. The plug is partially inserted into the lumen of the elongate tube at the distal end of the elongate tube to a first position. In the first position, the first end of the plug is located within the lumen of the elongate tube proximal of the distal end of the elongate tube a first distance. In the first position one or more fluid pathways are open for introducing a sterilization fluid from exterior of the elongate tube, past the plug and into the lumen of the elongate tube. With the plug in the first position, a sterilization fluid is introduced into the lumen of the elongate tube through the one or more fluid pathways to sterilize the medical catheter. After the step of introducing a sterilization fluid into the lumen of the elongate tube, the plug is further inserted into the lumen of the elongate tube to a second position. In the second position, the first end of the plug is located within the lumen of the elongate tube proximal of the distal end of the elongate tube a second distance greater than the first distance. In the second position, the distal end of the elongate tube is hermetically sealed with the plug, establishing a hermetically sealed environment within the elongate tube. In some embodiments, the plug may include an oxygen and/or moisture absorbing material. The oxygen and/or moisture absorbing material may be activated and/or exposed to the hermetically sealed environment when the plug is inserted into the lumen of the elongate tube.

The above summary of some example embodiments is not intended to describe each disclosed embodiment or every implementation of the invention.

BRIEF DESCRIPTION OF THE DRAWINGS

The invention may be more completely understood in consideration of the following detailed description of various embodiments in connection with the accompanying drawings, in which:

FIG. 1 is a perspective view of an exemplary plug and a distal portion of a carrier tube;

FIG. 1A is a transverse cross-sectional view of the carrier tube shown in FIG. 1 taken along line 1A-1A;

Figure 2A:
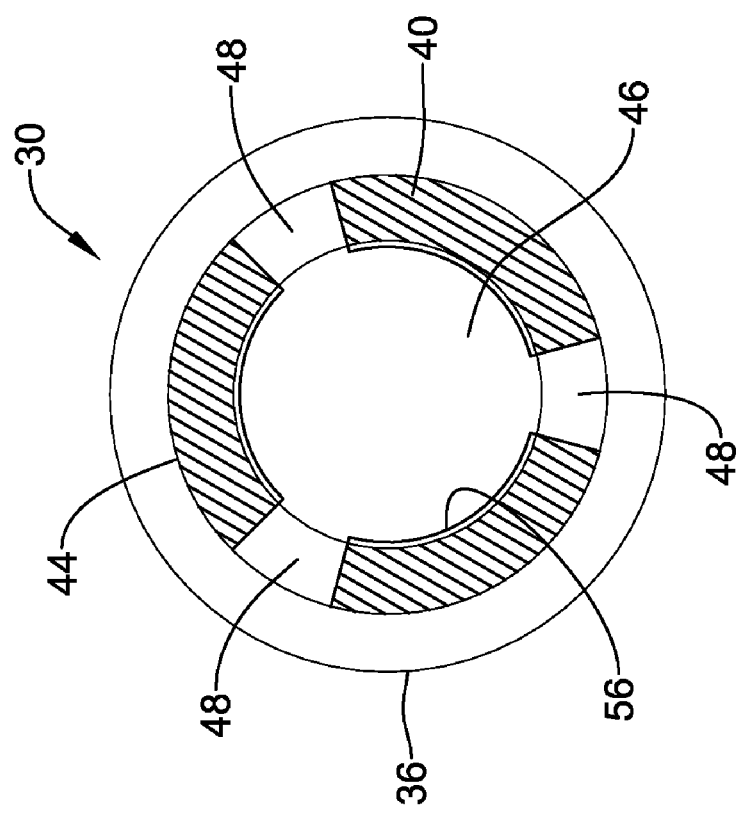
FIG. 2A is an alternative transverse cross-sectional view of the plug shown in FIG. 1 taken along line 2-2.

While the invention is amenable to various modifications and alternative forms, specifics thereof have been shown by way of example in the drawings and will be described in detail. It should be understood, however, that the intention is not to limit aspects of the invention to the particular embodiments described. On the contrary, the intention is to cover all modifications, equivalents, and alternatives falling within the spirit and scope of the invention.

DETAILED DESCRIPTION

For the following defined terms, these definitions shall be applied, unless a different definition is given in the claims or elsewhere in this specification.

All numeric values are herein assumed to be modified by the term "about", whether or not explicitly indicated. The term "about" generally refers to a range of numbers that one of skill in the art would consider equivalent to the recited value (i.e., having the same function or result). In many instances, the term "about" may be indicative as including numbers that are rounded to the nearest significant figure.

The recitation of numerical ranges by endpoints includes all numbers within that range (e.g., 1 to 5 includes 1, 1.5, 2, 2.75, 3, 3.80, 4, and 5).

Although some suitable dimensions ranges and/or values pertaining to various components, features and/or specifications are disclosed, one of skill in the art, incited by the present disclosure, would understand desired dimensions, ranges and/or values may deviate from those expressly disclosed.

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

The following detailed description should be read with reference to the drawings in which similar elements in different drawings are numbered the same. The detailed description and the drawings, which are not necessarily to scale, depict illustrative embodiments and are not intended to limit the scope of the invention. The illustrative embodiments depicted are intended only as exemplary. Selected features of any illustrative embodiment may be incorporated into an additional embodiment unless clearly stated to the contrary.

Referring now to FIG. 1, there is shown an embodiment of a carrier tube assembly 10 for packaging a medical device, for example, a balloon catheter such as a stent delivery catheter having a stent crimped to a balloon of the stent delivery catheter, or an angioplasty balloon catheter (POBA). In other embodiments, the medical device could be another medical device, such as an atherectomy device, an embolic protection device, an embolic coil delivery device, a sphinctertome, or the like. In some embodiments, the medical device may include a coating, such as a hydrophilic coating, a hydrophobic coating, a protective coating, a therapeutic coating, or other coating, covering at least a portion of the medical device, such as one or more components of the medical device. For example, the medical device may include a hydrophilic coating covering a distal portion of the elongate shaft and/or balloon of a catheter, and/or the medical device may include a stent having a therapeutic coating, such as a drug-eluting (i.e., drug releasing) coating.

Some such coatings which are applied to a medical device can be negatively affected by exposure to elevated levels of temperature, light, moisture, and/or oxygen. For example, some drug eluting coatings, such as synthetic bioerodible polyester polymers like poly(lactide-co-glycolide), also named PLG or PLGA, contain unstable linkages in their molecular backbone and become unstable and degrade (e.g., bioerode) when exposed to moisture through a hydrolysis process. Excipients, substances used as a carrier for therapeutic agents, may also be impacted by exposure to elevated levels of temperature, light, moisture, and/or oxygen. For example, poly vinyl pyrrolidone (PVP), which is used as an excipient, swells when exposed to water. As another example, some lubricious coatings, such as polyethylene oxide (PEO) are sensitive to water. Therefore it can be seen that properties and attributes of such coatings can be compromised and/or altered by exposure to undesirable levels of temperature, light, moisture, and/or oxygen. For example, shelf stability, device coating delivery durability, and coating degradation rate of drug eluting coatings for stents may be compromised by exposure to even very minute amounts of water and/or oxygen.

The carrier tube assembly 10 may sealingly surround at least a portion of the medical device, such as the portion of the medical device including the coating to provide a hermetically sealed environment for isolating the coating from exposure to elevated levels of temperature, light, moisture, and/or oxygen.

The carrier tube assembly 10 may include a carrier tube 12 (e.g., an elongate tube) having a proximal end 14 (shown in FIGS. 5A and 5B) and a distal end 16. The carrier tube 12 may be an elongate tubular member having a lumen 18 extending therethrough from the proximal end 14 to the distal end 16. The carrier tube 12 may have an annular wall 20 defining an inner surface 22 of the carrier tube 12 and an outer surface 24 of the carrier tube 12. The carrier tube 12 may be any desired length. For example, in some embodiments the carrier tube 12 may have a length greater than the length of the elongate shaft of a catheter, such that the entire elongate shaft of the catheter could be positioned within the lumen 18 of the carrier tube 12. In other embodiments, the carrier tube 12 may have a length less than the length of the elongate shaft of a catheter, such that the carrier tube 12 may be positioned over only a portion of the length of the elongate shaft, for example the distal portion of the elongate shaft of the catheter.

The carrier tube 12 may be formed from any desired material. For example, the carrier tube 12 may be formed of a polymeric material such as polyethylene, polyamide, or polyether block amide. However, other materials, including but not limited to other polymeric materials, may be used if desired.

The carrier tube assembly 10 may also include a plug 30. The plug 30, which in some embodiments may be a cylindrical plug, may include a first end 32 and a second end 34. As shown in FIG. 1, the plug 30 may include a head 36 proximate the second end 34 and a shank 38 extending from the head 36 to the first end 32 of the plug 30. In some embodiments, the head 36 may have a greater circumference or periphery than the circumference or periphery of the shank 38 of the plug 30. In some embodiments, the plug 30 may have a length between the first end 32 and the second end 34 of about 1 to about 5 inches, about 2 to about 4 inches, or about 2 to about 3 inches.

Figure 2:
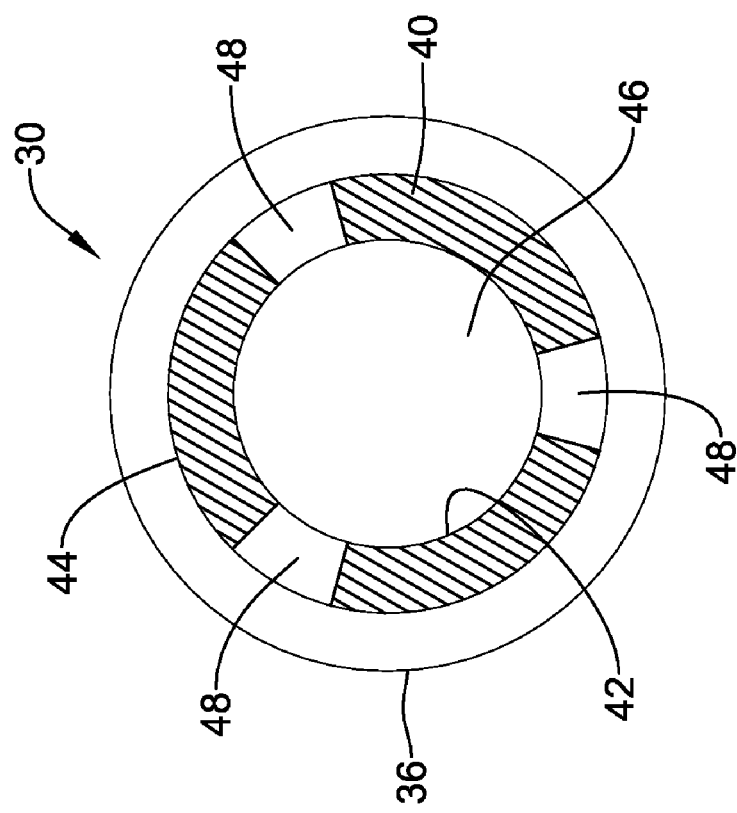
FIG. 2 is a transverse cross-sectional view of the plug shown in FIG. 1 taken along line 2-2.

As shown in the transverse cross-sectional view shown in FIG. 2, which is taken transverse to the longitudinal axis of the plug 30, the shank 38 of the plug 30 may include an annular wall 40 defining an interior surface 42 and an exterior surface 44. Thus, the shank 38 of the plug 30 may include a central bore 46 defined by the interior surface 42 of the plug 30. The central bore 46 may extend from the first end 32 of the plug 30 toward the second end 34. As shown in the longitudinal cross-sectional view of FIG. 3, the central bore 46 may not extend throughout the entire longitudinal length of the plug 30. For example, the head 36 of the plug 30 may be solid such that the central bore 46 does not extend through the head 36 of the plug 30 to the second end 34.

The plug 30 may include one or more, or a plurality of openings 48 extending through the annular wall 40 of the plug 30 from the exterior surface 44 to the interior surface 42. Thus, the openings 48 may extend into the central bore 46 of the shank 38 of the plug 30 through the annular wall 40 of the shank 38. For example, the plug 30 may include one, two, three, four, or more openings 48 extending through the annular wall 40 into the central bore 46 of the plug 30. In one embodiment, shown in FIG. 1, the openings 48 may be elongate slots 50 which may have a longitudinal length greater than a peripheral width. In other embodiments, the openings 48 may be circular, oval, helical, or any other desired shape extending through the annular wall 40 of the plug 30. As shown in FIG. 1, each of the elongate slots 50 may extend over a majority of the length of the shank 38. For example, each elongate slot 50 may extend over 50% or more, 60% or more, 70% or more, 80% or more or 90% or more of the length of the shank 38. In other embodiments, one or more, or a plurality of openings 48 may be located at one or more, or a plurality of spaced apart locations along the longitudinal length of the shank 38.

As shown in FIG. 2, in some embodiments, a plurality of openings 48 may be equally spaced around the circumference of the annular wall 40 of the shank 38. For example, three openings 48 may be equally spaced at 120° increments around the circumference of the shank 38 of the plug 30. In other embodiments, four openings 48 may be equally spaced at 90° increments around the circumference of the shank 38 of the plug 30. Other possible arrangements for the openings 48 may be achieved if desired.

Figure 3:
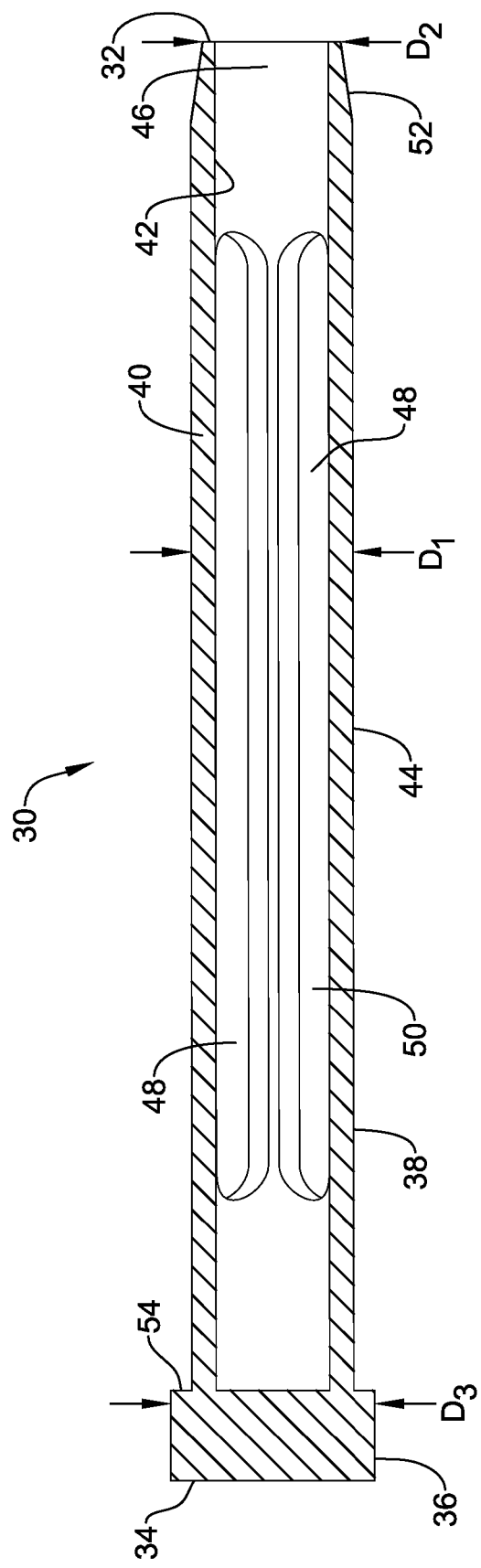
FIG. 3 is a longitudinal cross-sectional view of the plug shown in FIG. 1 taken along line 3-3.
Figure 3A:
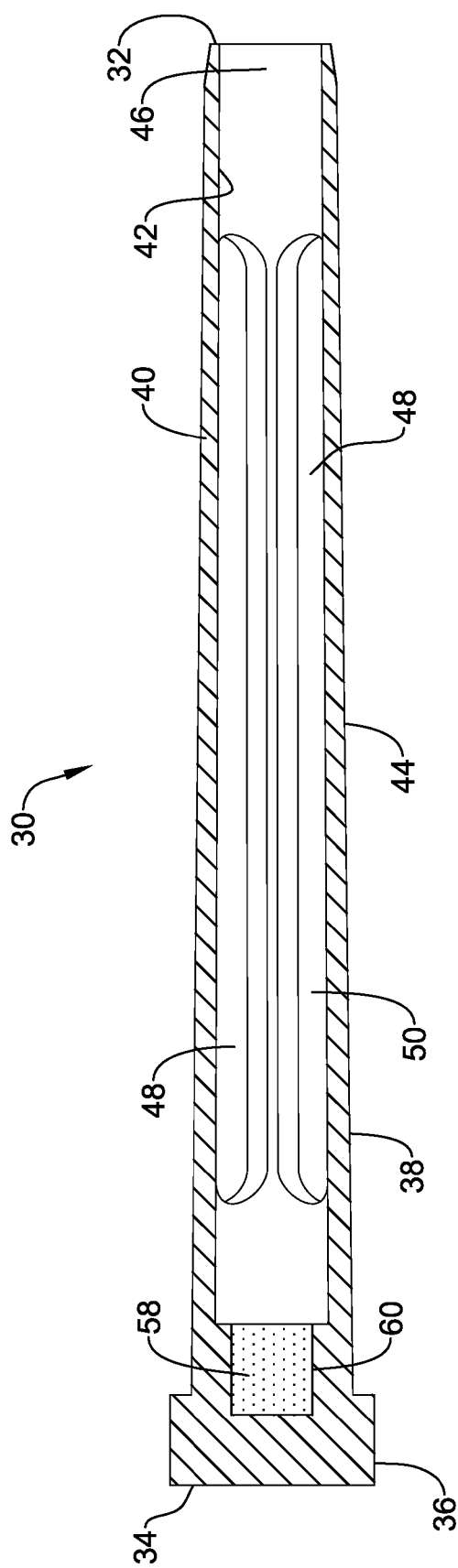
FIG. 3A is an alternative longitudinal cross-sectional view of the plug shown in FIG. 1 taken along line 3-3.

As shown in FIG. 3, the shank 38 of the plug 30 may have an outside diameter $D_1$ which is greater than the inside diameter of the carrier tube 12. Thus, when the shank 38 of the plug 30 is inserted into the distal end 16 of the carrier tube 12 an interference fit is established between the exterior surface 44 of the shank 38 and the inner surface 22 of the carrier tube. In some embodiments, the shank 38 of the plug 30 may have a constant outer diameter along a portion of, along a majority of, or along a substantial portion of the length of the shank 38. In other embodiments, such as shown in FIG. 3A, the outside diameter $D_1$ of the shank 38 of the plug 30 may vary continuously along a portion of, along a majority of, or along a substantial portion of the length of the shank 38. For example, the thickness of the annular wall 40 of the plug 30 shown in FIG. 3A may vary continuously along 25% or more, 50% or more, or 75% or more of the length of the shank 38. The plug 30, as shown in FIG. 3 may include a tapered end 52, such that the outside diameter $D_2$ of the shank 38 at the first end 32 is less than the outside diameter $D_1$ of the shank 38 at a location closer to the head 36 of the plug 30. In some embodiments, the outside diameter $D_2$ of the shank 38 at the first end 32 may be less than the inside diameter of the carrier tube 12 at the distal end 16 of the carrier tube 12 to facilitate insertion of the plug 30 into the carrier tube 12.

The head 36 of the plug 30 may have an outer diameter $D_3$ greater than the outside diameter $D_1$ of the shank 38, thus creating a flange 54. In some embodiments, the outer diameter $D_3$ may be greater than the inside diameter of the carrier tube 12 such that the head 36 of the plug 30 will not extend into the carrier tube 12. Thus, when the plug 30 is fully inserted into the carrier tube 12, the flange 54 of the head 36 may abut the distal end 16 of the carrier tube 12. In some embodiments, the outer diameter $D_3$ may be less than, equal to, or greater than the outside diameter of the carrier tube 12.

The plug 30 may be formed of any desired material. For example, the plug 30 may be formed of polymeric material such as polyethylene, polyamide, or polyether block amide. However, other materials, including but not limited to other polymeric materials, may be used if desired.

In some embodiments, such as shown in FIG. 1, the plug 30 may include an oxygen and/or moisture absorbing substance incorporated into the material of the plug 30. In other words, in some embodiments an oxygen and/or moisture absorbing substance may be dispersed throughout the molecular structure of the material of the plug 30. Dispersion of an oxygen and/or moisture absorbing substance throughout the material of the plug 30 may be conducted during formation of the plug, for example, during a molding process or an extrusion process.

In some embodiments the oxygen and/or moisture absorbing substance may be a desiccant, an oxygen scavenger, a cyclodextrin, or other desired substance. Some possible desiccants include activated alumina, aerogel, calcium chloride, calcium hydride, calcium sulfate, and silica gel.

In other embodiments, such as shown in FIG. 2A, the plug 30 may include an additional layer 56 including an oxygen and/or moisture absorbing substance. The layer of material 56 including the oxygen and/or moisture absorbing substance may be located on the interior of the annular wall 40 of the shank 38 of the plug 30 or at another location of the plug 30.

FIG. 3A shows another embodiment of the plug 30 including a core of material 58 including an oxygen and/or moisture absorbing substance. As shown in FIG. 3A, the core 58 may be formed of a first material and the outer portion of the plug 30 (e.g., the shank 38 and/or head 36) may be formed of a second material different from the first material. The core 58 may be located in a counter-bored hole 60 formed in the interior of the plug 30. For example, the counter-bored hole 60 containing the core 58 may be formed in a portion of the plug 30 proximate the head 36 of the plug 30 at the end of the central bore 46 closest to the second end 34 of the plug 30. In some embodiments, the counter-bored hole 60, and thus the core 58, may be coaxial with the central bore 46. With the core 58 positioned in the counter-bored hole 60, at least one surface of the core 58 may be exposed to the central bore 46 of the plug 30.

Figure 3B:
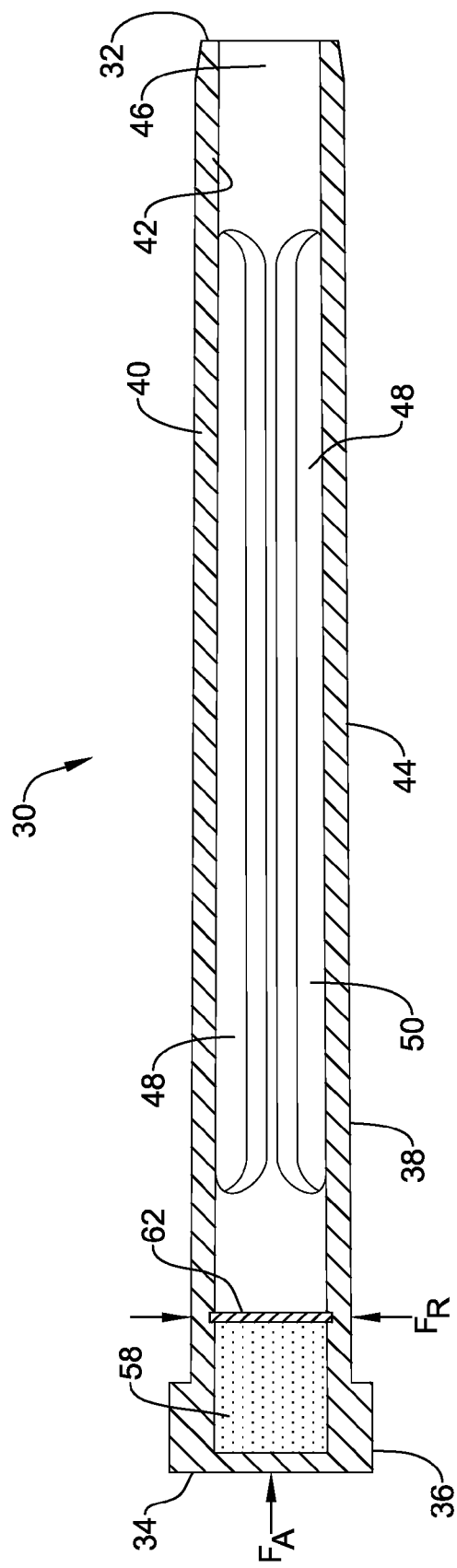
FIG. 3B is another alternative longitudinal cross-sectional view of the plug shown in FIG. 1 taken along line 3-3.

FIG. 3B shows yet another embodiment of the plug 30 including a core of material 58 including an oxygen and/or moisture absorbing substance similar to that shown in FIG. 3A. As shown in FIG. 3B, a frangible layer of material 62 is located on one side of the core 58, separating the core 58 from the central bore 46 of the plug 30. When the plug 30 shown in FIG. 3B is inserted into the distal end of the carrier tube 12, the frangible layer of material 62 may separate the core 58 from the hermetically sealed environment established within the carrier tube 12. The frangible layer of material 62 may be selectively broken when desired to expose the core 58 to the hermetically sealed environment, and thus activate the core 58 to absorb oxygen and/or moisture within the hermetically sealed environment.

For instance, in some embodiments an axial force $F_A$ could be applied to the head 36 of the plug 30 in order to crack, break, separate or otherwise divide portions of the frangible layer 62 to expose the core 58 to the central bore 46 of the plug 30, and thus to the hermetically sealed environment, through one or more openings formed through the frangible layer 62. The force $F_A$ could be applied before the plug 30 is inserted into the carrier tube 12, the force $F_A$ could be applied as the plug 30 is being inserted into the carrier tube 12, or the force $F_A$ could be applied subsequent to fully inserting the plug 30 in the carrier tube 12.

Additionally or alternatively, an inward radial force $F_R$ could be applied to the plug 30 in order to crack, break, separate or otherwise divide portions of the frangible layer 62 to expose the core 58 to the central bore 46 of the plug 30, and thus to the hermetically sealed environment, through one or more openings formed through the frangible layer 62. The force $F_R$ could be applied before the plug 30 is inserted into the carrier tube 12, the force $F_R$ could be applied as the plug 30 is being inserted into the carrier tube 12, or the force $F_R$ could be applied subsequent to fully inserting the plug 30 in the carrier tube 12. In some embodiments, the force $F_R$ could be the radial compressive force exerted on the plug 30 by the carrier tube 12 through the interference fit established between the plug 30 and the carrier tube 12. In other words, in some embodiments the force $F_R$ may be generated as the plug 30 is pushed into the lumen 18 of the carrier tube 12, cracking, breaking, separating or otherwise dividing portions of the frangible layer 62 as the carrier tube 12 moves over the shank 38 of the plug 30 proximate the frangible layer 62.

Other means may also be utilized to selectively activate and/or expose the oxygen and/or moisture absorbing substance to absorb oxygen and/or moisture within the hermetically sealed environment. For instance, a chemical reaction, electromagnetic radiation, or other stimulus may be used to selectively activate and/or expose the oxygen and/or moisture absorbing substance to absorb oxygen and/or moisture within the hermetically sealed environment.

Figure 4:
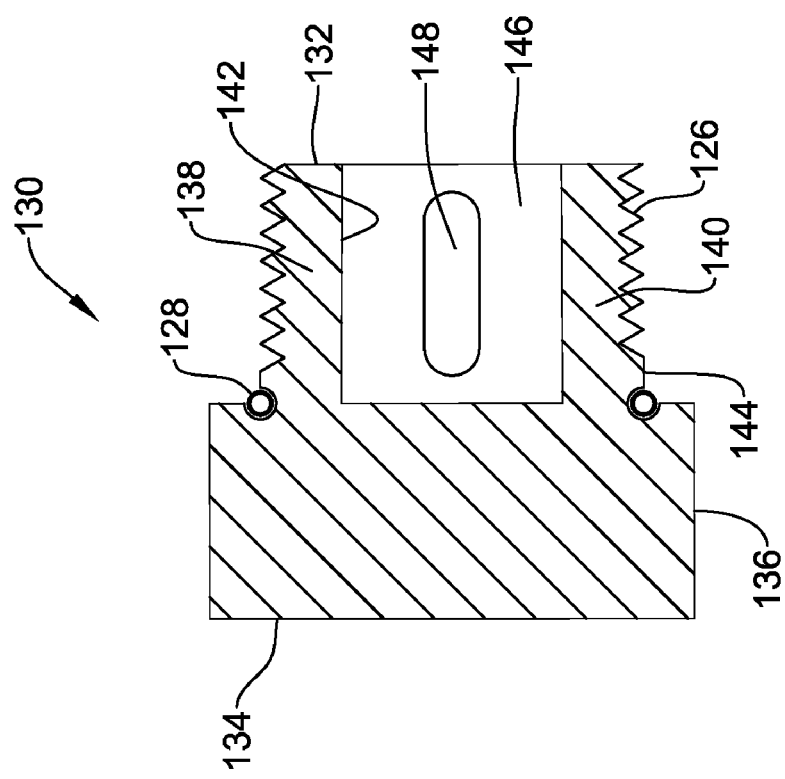
FIG. 4 is another exemplary embodiment of a plug for use with a carrier tube.

Another embodiment of a plug 130 which could be used to provide a hermetic seal at the distal end 16 of the carrier tube 12 is illustrated in FIG. 4. The plug 130 extends from a first end 132 to a second end 134. As shown in FIG. 4, the plug 130 may include a head 136 proximate the second end 134 and a shank 138 extending from the head 136 to the first end 132 of the plug 130. In some embodiments, the head 136 may have a greater circumference than the circumference of the shank 138 of the plug 130.

The shank 138 of the plug 130 may include an annular wall 140 defining an interior surface 142 and an exterior surface 144. Thus, the shank 138 of the plug 130 may include a central bore 146 defined by the interior surface 142 of the plug 130. The central bore 146 may extend from the first end 132 of the plug 130 toward the second end 134. However, the central bore 146 may not extend throughout the entire longitudinal length of the plug 130. For example, the head 136 of the plug 130 may be solid such that the central bore 146 does not extend through the head 136 of the plug 130 to the second end 134.

The plug 130 may include one or more, or a plurality of openings 148 extending through the annular wall 140 of the plug 130 from the exterior surface 144 to the interior surface 142. Thus, the openings 148 may extend into the central bore 146 of the shank 138 of the plug 130 through the annular wall 140 of the shank 138. For example, the plug 130 may include one, two, three, four, or more openings 148 extending through the annular wall 140 into the central bore 146 of the plug 130. In one embodiment, the openings 148 may be elongate slots which may have a longitudinal length greater than a peripheral width. In other embodiments, the openings 148 may be circular, oval, helical, or any other desired shape extending through the annular wall 140 of the plug 130. In some embodiments, the openings 148 may extend over a majority of the length of the shank 138. For example, the openings 148 may extend over 50% or more, 60% or more, 70% or more, 80% or more or 90% or more of the length of the shank 138. In other embodiments, one or more, or a plurality of openings 148 may be located at one or more, or a plurality of locations spaced apart along the longitudinal length of the shank 138.

In some embodiments, a plurality of openings 148 may be equally spaced around the circumference of the annular wall 140 of the shank 138. For example, three openings 148 may be equally spaced at 120° increments around the circumference of the shank 138 of the plug 130. In other embodiments, four openings 148 may be equally spaced at 90° increments around the circumference of the shank 138 of the plug 130. Other possible arrangements for the openings 148 may be achieved if desired.

The shank 138 may include threads 126 formed in the exterior surface 144 of the plug 130 (i.e., a male threaded portion). The threads 126 of the plug 130 may threadedly engage with complementary threads formed in the inner surface 22 of the carrier tube 12 (i.e., a female threaded portion). In such an embodiment, the plug 130 may be screwed into the lumen 18 of the carrier tube 12 to hermetically seal the distal end 16 of the carrier tube 12. In some embodiments, the plug 130 may include an annular seal 128, such as an O-ring or gasket, at the interface between the plug 130 and the carrier tube 12 to help form a seal between the plug 130 and the carrier tube 12. It is to be noted that in other embodiments, the plug 130 may include a female threaded portion having threads on an interior surface and the carrier tube 12 may include a complementary male threaded portion having threads on the outer surface 24 of the carrier tube 12.

Although the plug 30 has been illustrated as being inserted into the lumen 18 of the carrier tube 12, one of skill in the art would understand that in other embodiments a plug surrounding the distal end 16 of the carrier tube 12 and sealing the lumen 18 could also be used. For example, a cap, such as a press-fit or threaded cap, could be placed over the distal end 16 of the carrier tube 12 to provide a hermetic seal at the distal end 16 of the carrier tube 12. In yet other embodiments, a plug having a first portion inserted into the lumen 18 of the carrier tube 12 and in contact with the inner surface 22 of the carrier tube 12, and a second portion disposed over the carrier tube 12 and in contact with the outer surface 24 of the carrier tube 12 could be used.

Figure 5A:
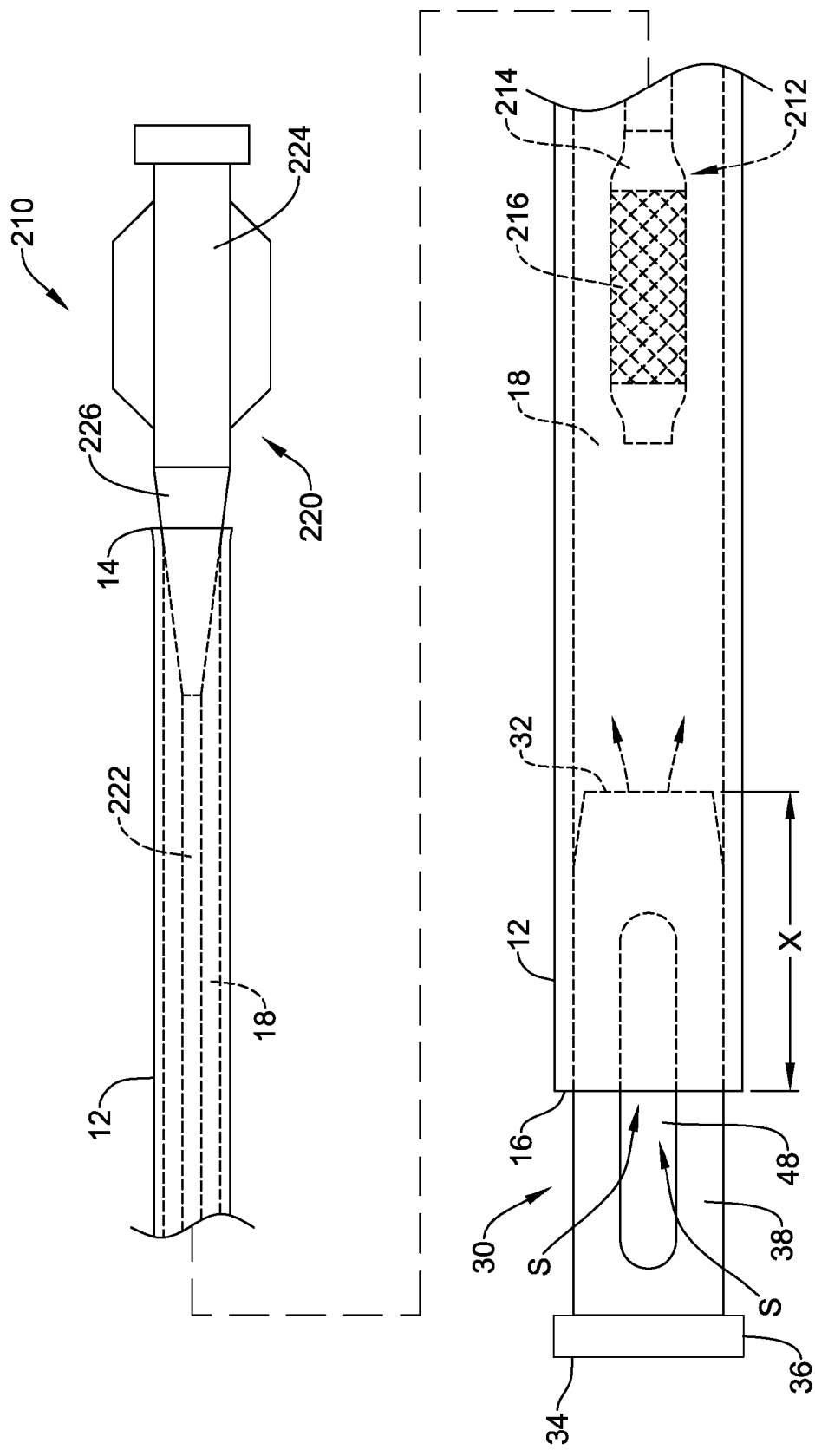
FIGS. 5A and 5B illustrate an exemplary process of sterilizing the contents in a carrier tube prior to hermetically sealing the carrier tube.
Figure 5B:
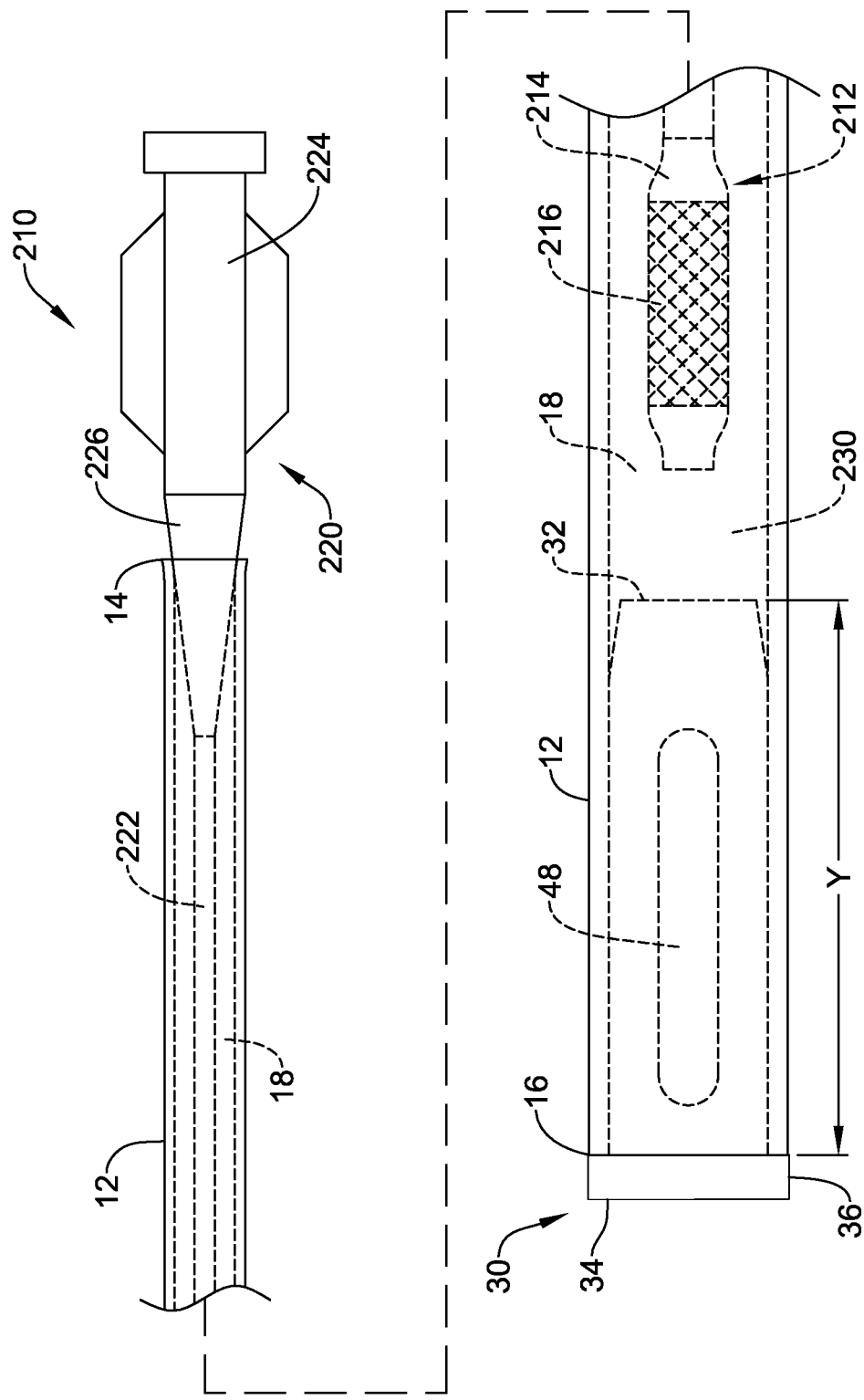

When packaging a medical device, such as a catheter, within the carrier tube 12 it may be desirable to sterilize the medical device. Thus, the medical device may be hermetically sealed in a sterilized environment within the carrier tube 12. FIGS. 5A and 5B demonstrate one possible method of packaging and sterilizing a catheter 210 within the carrier tube 12.

As shown in FIG. 5A, at least a portion of the catheter 210 may be inserted into the lumen 18 of the carrier tube 12. As shown in FIG. 5A, the catheter 210 may include a hub assembly 220 and an elongate shaft 222. The hub assembly 220 may include a hub 224 and a strain relief 226 providing a transition region between the hub 224 and the elongate shaft 222 to prevent kinking of the elongate shaft 222 proximate the hub 220. The elongate shaft 222 of the catheter 210 may include an inflation balloon 214 and/or a stent 216 located in the distal region of the elongate shaft 222. In some embodiments, the elongate shaft 222 may include a coating, such as a hydrophilic coating over a portion of the length of the elongate shaft 222 and/or the stent 216 may include a coating, such as a drug-eluting coating.

The elongate shaft 222, or at least a distal portion thereof, may be inserted into the lumen 18 of the carrier tube 12. As shown in FIG. 5A, the proximal end 14 of the carrier tube 12 may be sealingly engaged around a portion of the hub assembly 220 of the catheter 210. For example, the proximal end 14 of the carrier tube 12 may be hermetically sealed around the strain relief 226 of the catheter 210. In some embodiments, the proximal end 14 of the carrier tube 12 may be flared radially outward or caused to be flared radially outward when circumferentially engaged around the strain relief 226 or other portion of the hub assembly 220. In some embodiments the proximal end 14 of the carrier tube 12 may be press fit around the strain relief 226 or other portion of the hub assembly 220, and/or the carrier tube 12 may include a seal, such as an O-ring or gasket, at the interface between the carrier tube 12 and the strain relief 226 or other portion of the hub assembly 220. In some embodiments, the proximal end 14 of the carrier tube 12 may include a threaded portion for threaded engagement with a portion of the hub assembly 220 of the catheter 210 and/or a funneled or necked region for engagement with a portion of the hub assembly 220.

As further shown in FIG. 5A, with the proximal end 14 of the carrier tube 12 hermetically sealed around the hub assembly 220 of the catheter 210, the distal end region 212 of the catheter 210, including the inflation balloon 214 and the stent 216, is located within the lumen 18 of the carrier tube 12 proximate the distal end 16 of the carrier tube 12.

The plug 30 may be partially inserted into the lumen 18 of the carrier tube 12 at the distal end 16 of the carrier tube 12 to a first position. In the first position, shown in FIG. 5A, the first end 32 of the plug 30 is located within the lumen 18 of the carrier tube 12 proximal of the distal end 16 of the carrier tube 12 a first distance X. With the plug 30 partially inserted into the carrier tube 12 at the first position, at least a portion of the openings 48 of the plug 30 are not covered by the carrier tube 12, and remain exposed to the ambient environment exterior of the carrier tube 12. With at least a portion of the openings 48 remaining uncovered, one or more fluid pathways are defined from exterior of the carrier tube 12 into the lumen 18 of the carrier tube 12. In the embodiment shown in FIG. 5A, the one or more fluid pathways are defined through the openings 48 of the plug 30, into the central bore 46 of the plug 30, which provides fluid access to the lumen 18 of the carrier tube 12.

As shown by the arrows in FIG. 5A, with the plug 30 partially inserted into the carrier tube 12, a sterilization fluid S, such as ethylene oxide, may be introduced into the lumen 18 of the carrier tube 12 from exterior of the carrier tube 12 through the uncovered openings 48 extending through the annular wall 40 of the plug 30 into the central bore 46 and into the lumen 18 of the carrier tube 12. The sterilization fluid S may be introduced through the fluid pathways to sterilize the catheter 210 disposed in the carrier tube 12.

After a desired quantity of the sterilization fluid S has been introduced into the lumen 18 of the carrier tube 12, the plug 30 may be further inserted into the lumen 18 of the carrier tube 12 to a second position, as shown in FIG. 5B. In the second position, the first end 32 of the plug 30 is located within the lumen 18 of the carrier tube 12 proximal of the distal end 16 of the carrier tube 12 a second distance Y which is greater than the first distance X. In some embodiments, the second position may be considered a position in which the plug 30 is fully inserted into the lumen 18 at the distal end 16 of the carrier tube 12, such that the head 36 of the plug 30 abuts the distal end 16 of the carrier tube 12.

With the plug 30 inserted to the second position shown in FIG. 5B, the openings 48 through the annular wall 40 of the plug 30 are covered by the carrier tube 12 and the distal end 16 of the carrier tube 12 is hermetically sealed by the plug 30. An interference fit may be established between the exterior surface 44 of the plug 30 and the inner surface 22 of the carrier tube 12 to hermetically seal the distal end 16 of the carrier tube 12. In some embodiments, an annular seal, such as an O-ring or gasket, may be present to facilitate establishing a hermetical seal at the distal end 16 of the carrier tube 12.

With the proximal end 14 of the carrier tube 12 hermetically sealed around a portion of the hub assembly 220 of the catheter 210 and the distal end 16 of the carrier tube 12 hermetically sealed by the plug 30, a hermetically sealed environment 230 is established within the lumen 18 of the carrier tube 12. The distal end region 212 of the catheter 210, for example, the elongate shaft 220, the inflation balloon 214 and/or the stent 216 may be exposed to the hermetically sealed environment 230 within the carrier tube 12. The hermetically sealed environment 230 may be a sterilized environment around the portion of the catheter 210 located within the lumen 18 of the carrier tube 12.

In embodiments in which the plug 30 includes an oxygen and/or moisture absorbing substance, the oxygen and/or moisture absorbing substance may be exposed to the hermetically sealed environment 230 formed within the carrier tube 12. Thus, the oxygen and/or moisture absorbing substance may absorb oxygen and/or moisture present in the hermetically sealed environment 230, and thus reduce the level of oxygen and/or moisture found in the hermetically sealed environment 230. Thus, the oxygen and/or moisture absorbing substance may preserve the integrity of any coatings which may be applied to a portion of the catheter 210, such as a coating applied to the elongate shaft 222 and/or balloon 214, and/or a coating applied to the stent 216, as discussed above.

In some embodiments, the oxygen and/or moisture absorbing substance may be selectively activated and/or selectively exposed to the hermetically sealed environment 230 prior to inserting the plug 30 into the lumen 18 of the carrier tube 12, as the plug 30 is inserted into the lumen 18 of the carrier tube 12, or after the plug 30 has been inserted into the lumen 18 of the carrier tube 12. For example, as discussed above, a frangible layer of material 62 separating the oxygen and/or moisture absorbing substance from the hermetically sealed environment 230 may be selectively broken when desired to expose the oxygen and/or moisture absorbing substance to the hermetically sealed environment 230, and thus activate the oxygen and/or moisture absorbing substance to absorb oxygen and/or moisture within the hermetically sealed environment 230.

In other embodiments, other means may also be utilized to selectively activate and/or expose the oxygen and/or moisture absorbing substance to absorb oxygen and/or moisture within the hermetically sealed environment 230. For instance, a chemical reaction, electromagnetic radiation, or other stimulus may be used to selectively activate and/or expose the oxygen and/or moisture absorbing substance to absorb oxygen and/or moisture within the hermetically sealed environment 230.

As shown in FIG. 5B, when the plug 30 is fully inserted into the carrier tube 12 to establish the hermetically sealed environment 230, the first end 32 of the plug 30 may be located proximate to the distal end of the catheter 210, and thus proximate to the inflation balloon 214 and/or the stent 216. For example, the first end 32 of the plug 30 may be located within about 5 inches, within about 4 inches, within about 3 inches, within about 2 inches, or within about 1 inch of the distal end of the catheter 210. Thus, the oxygen and/or moisture absorbing substance, if present, may be close to the stent 216, for example, to absorb oxygen and/or moisture in the hermetically sealed environment 230 adjacent the stent 216.

It is to be noted that in other embodiments a sterilization fluid, such as ethylene oxide, may be introduced into the lumen 18 of the carrier tube 12 prior to placing the plug 30 into the lumen 18 of the carrier tube 12. In yet other embodiments, the portion of the catheter 210 located within the confines of the carrier tube 12 may be sterilized after the hermetically sealed environment 230 within the carrier tube 12 has been established when the plug 30 has been inserted into the lumen 18 of the carrier tube 12 at the distal end 16 of the carrier tube 12. For example, in such an embodiment, sterilization may be accomplished using gamma radiation or electron beam (E-beam) sterilization.

Figure 6:
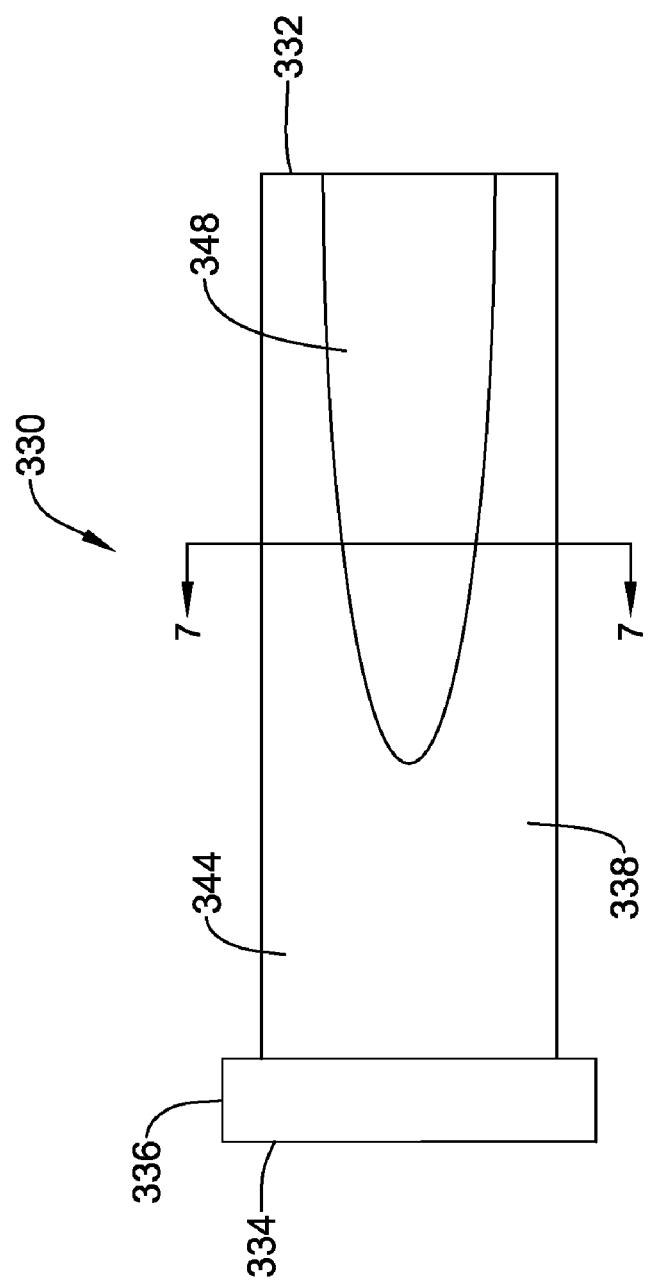
FIG. 6 is another exemplary embodiment of a plug for use with a carrier tube.

Another plug 330 which may be used in the carrier tube assembly 10 to hermetically seal the distal end 16 of the carrier tube 12 containing a medical device is shown in FIG. 6. The plug 330, which in some embodiments may be a cylindrical plug, may include a first end 332 and a second end 334. As shown in FIG. 6, the plug 330 may include a head 336 proximate the second end 334 and a shank 338 extending from the head 336 to the first end 332 of the plug 330.

Figure 7:
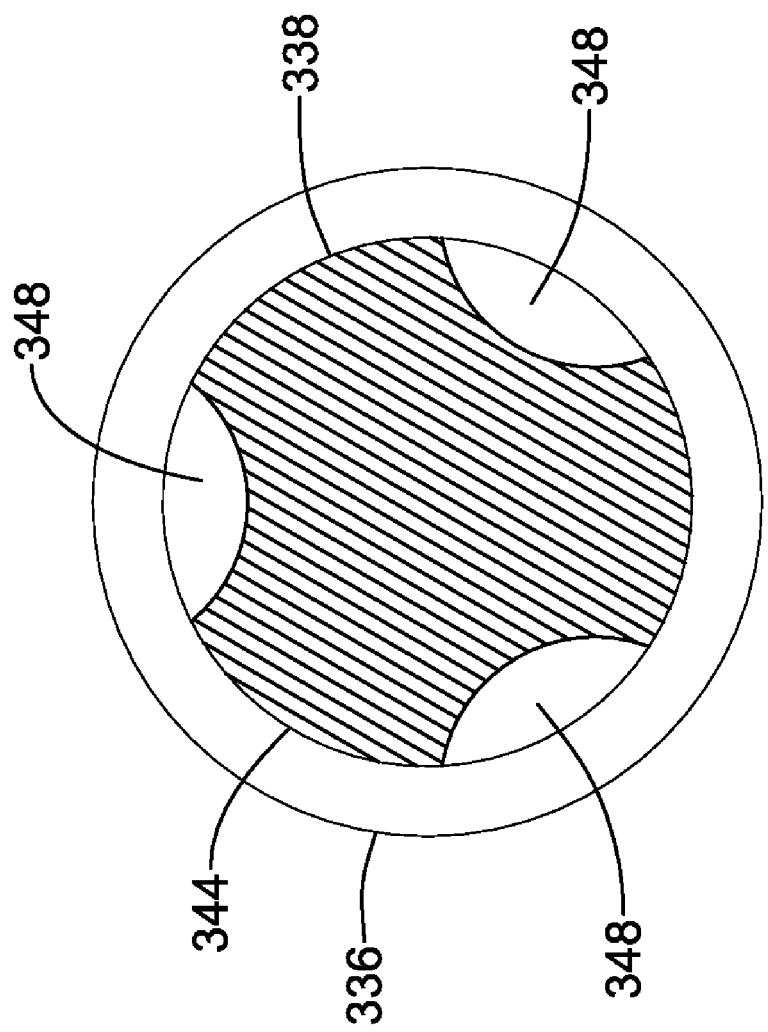
FIG. 7 is a transverse cross-sectional view of the plug shown in FIG. 6 taken along line 7-7.

The shank 338 of the plug 330 may include a generally circumferential exterior surface 344. Furthermore, the plug 330 may include one or more, or a plurality of recesses 348 in the exterior surface 344 of the shank 338. As shown in FIG. 7, in some embodiments the recesses 348 may be concave grooves or flutes. The recesses 348 may extend along the exterior surface 344 from the first end 332 of the plug 330 toward the second end 334. Thus, the shank 338 of the plug 330 may have a discontinuous circumferential exterior surface 344 proximate the first end 332 of the plug 330 and may have a continuous circumferential exterior surface 344 proximate the head 336 of the plug 330.

As shown in FIG. 7, in some embodiments, a plurality of recesses 348, such as concave grooves, flutes or other recesses, may be equally spaced around the circumference of the exterior surface 344 of the shank 338. For example, three recesses 348 may be equally spaced at 120° increments around the circumference of the shank 338 of the plug 330. In other embodiments, four recesses 348 may be equally spaced at 90° increments around the circumference of the shank 338 of the plug 330. Other possible arrangements for the recesses 348 may be achieved if desired.

Similar to the plug 30 discussed above, the plug 330 may be formed of any desired material, such as but not necessarily limited to a polymeric material. Additionally, the plug 330 may include an oxygen and/or moisture absorbing substance incorporated into the material of the plug 330, may include a layer of an oxygen and/or moisture absorbing substance, and/or may include a core of an oxygen and/or moisture absorbing substance.

Figure 8A:
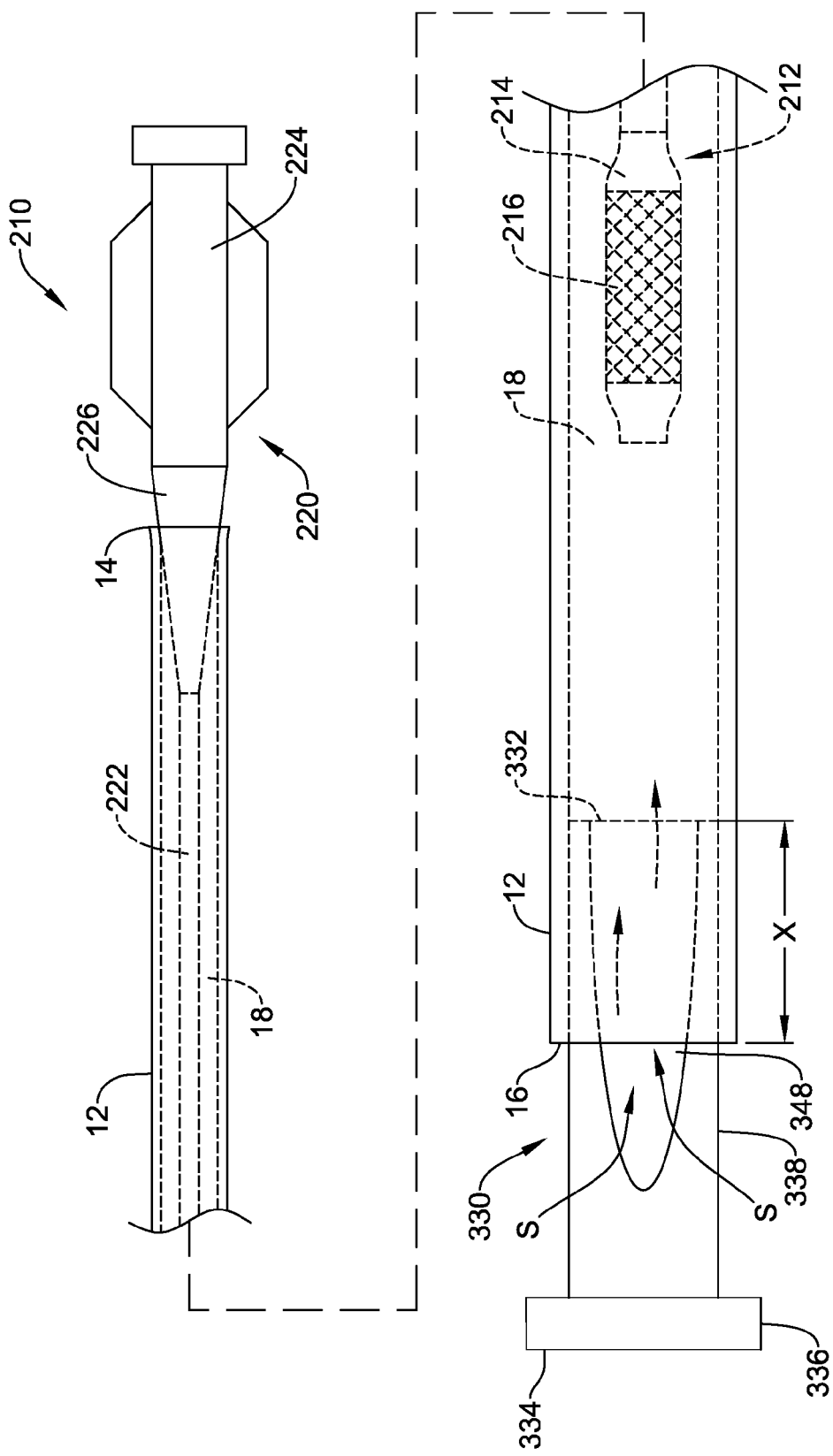
FIGS. 8A and 8B illustrate another exemplary process of sterilizing the contents in a carrier tube prior to hermetically sealing the carrier tube.
Figure 8B:
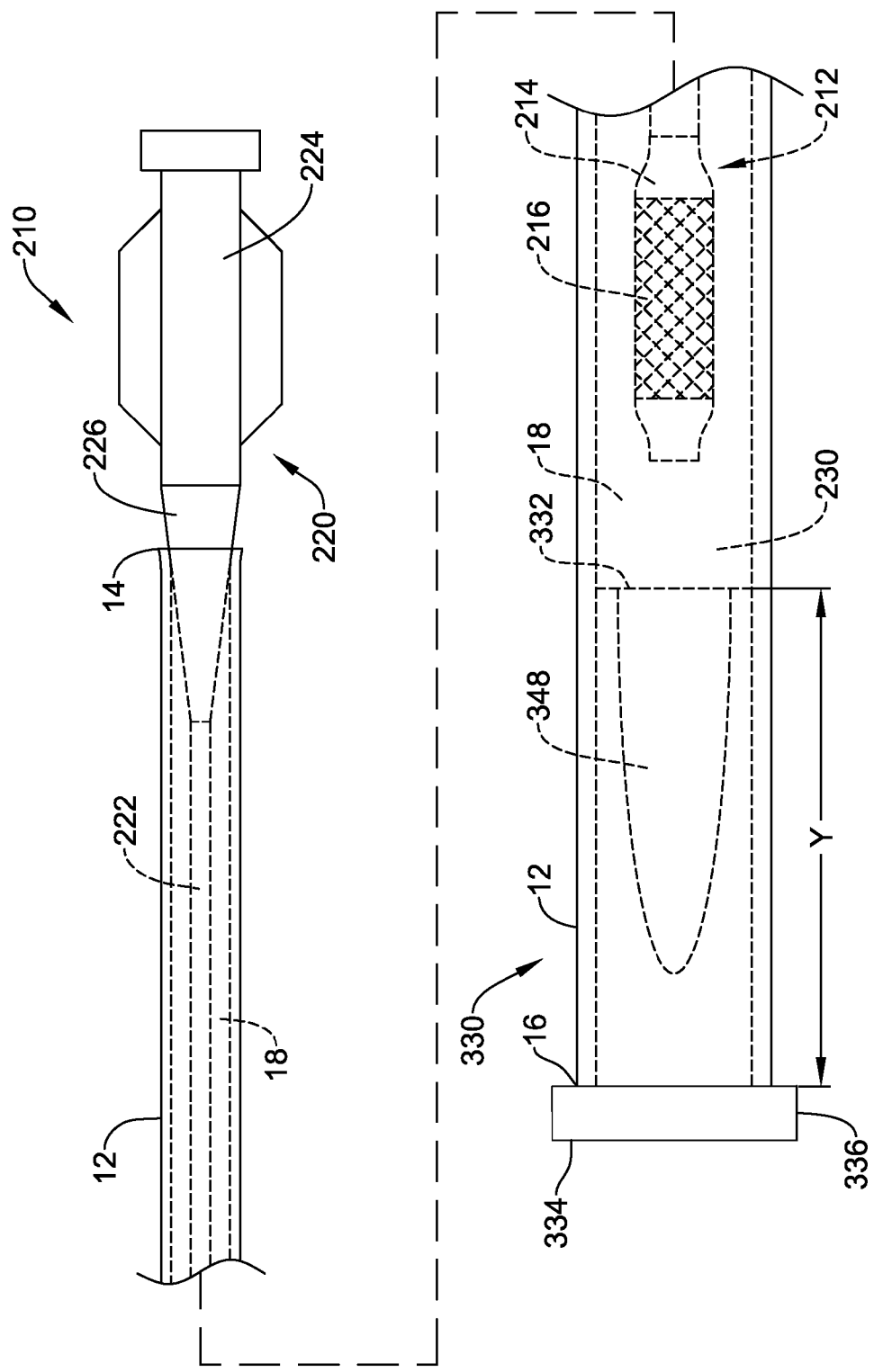

A method of using the plug 330 when packaging a medical device, such as the catheter 210, within the carrier tube 12 is illustrated in FIGS. 8A and 8B. As shown in FIG. 8A, at least a portion of the catheter 210 may be inserted into the lumen 18 of the carrier tube 12 and a hermetical seal may be established between the carrier tube 12 and a portion of the hub assembly 220 of the catheter 210 as discussed above. In some embodiments, the elongate shaft 222 may include a coating, such as a hydrophilic coating over a portion of the length of the elongate shaft 222 and/or the stent 216 may include a coating, such as a drug-eluting coating.

As further shown in FIG. 8A, with the proximal end 14 of the carrier tube 12 hermetically sealed around the hub assembly 220 of the catheter 210, the distal end region 212 of the catheter 210, including the inflation balloon 214 and the stent 216, is located within the lumen 18 of the carrier tube 12 proximate the distal end 16 of the carrier tube 12.

The plug 330 may be partially inserted into the lumen 18 of the carrier tube 12 at the distal end 16 of the carrier tube 12 to a first position. In the first position, shown in FIG. 8A, the first end 332 of the plug 330 is located within the lumen 18 of the carrier tube 12 proximal of the distal end 16 of the carrier tube 12 a first distance X. With the plug 330 partially inserted into the carrier tube 12 at the first position, at least a portion of the recesses 348, such as concave grooves or flutes, of the plug 330 are not covered by the carrier tube 12, and remain exposed to the ambient environment exterior of the carrier tube 12. With at least a portion of the recesses 348 remaining uncovered, one or more fluid pathways are defined from exterior of the carrier tube 12 into the lumen 18 of the carrier tube 12. In the embodiment shown in FIG. 8A, the one or more fluid pathways are defined from exterior of the carrier tube 12 through the recesses 348 defined between the exterior surface 344 of the plug 330 and the inner surface 22 of the carrier tube 12, which provides fluid access to the lumen 18 of the carrier tube 12.

As shown by the arrows in FIG. 8A, with the plug 330 partially inserted into the carrier tube 12, a sterilization fluid S, such as ethylene oxide, may be introduced into the lumen 18 of the carrier tube 12 from exterior of the carrier tube 12 through the recesses 348 defined between the exterior surface 344 of the plug 330 and the inner surface 22 of the carrier tube 12 and into the lumen 18 of the carrier tube 12. The sterilization fluid S may be introduced through the fluid pathways to sterilize the catheter 210 disposed in the carrier tube 12.

After a desired quantity of the sterilization fluid S has been introduced into the lumen 18 of the carrier tube 12, the plug 330 may be further inserted into the lumen 18 of the carrier tube 12 to a second position, as shown in FIG. 8B. In the second position, the first end 332 of the plug 330 is located within the lumen 18 of the carrier tube 12 proximal of the distal end 16 of the carrier tube 12 a second distance Y which is greater than the first distance X. In some embodiments, the second position may be considered a position in which the plug 330 is fully inserted into the lumen 18 at the distal end 16 of the carrier tube 12, such that the head 336 of the plug 330 abuts the distal end 16 of the carrier tube 12.

With the plug 330 inserted to the second position shown in FIG. 8B, the recesses 348 in the exterior surface 344 of the shank 338 of the plug 330 are covered by the carrier tube 12 and the distal end 16 of the carrier tube 12 is hermetically sealed by the plug 330. An interference fit may be established between the exterior surface 344 of the plug 330 and the inner surface 22 of the carrier tube 12 to hermetically seal the distal end 16 of the carrier tube 12. In some embodiments, an annular seal, such as an O-ring or gasket, may be present to facilitate establishing a hermetical seal at the distal end 16 of the carrier tube 12.

Similar to that discussed above regarding FIGS. 5A and 5B, with the proximal end 14 of the carrier tube 12 hermetically sealed around a portion of the hub assembly 220 of the catheter 210 and the distal end 16 of the carrier tube 12 hermetically sealed by the plug 330, a hermetically sealed environment 230 is established within the lumen 18 of the carrier tube 12. The distal end region 212 of the catheter 210, for example, the elongate shaft 220, the inflation balloon 214 and/or the stent 216 may be exposed to the hermetically sealed environment 230 within the carrier tube 12. The hermetically sealed environment 230 may be a sterilized environment around the portion of the catheter 210 located within the lumen 18 of the carrier tube 12.

In embodiments in which the plug 330 includes an oxygen and/or moisture absorbing substance, the oxygen and/or moisture absorbing substance may be exposed to the hermetically sealed environment 230 formed within the carrier tube 12. Thus, the oxygen and/or moisture absorbing substance may absorb oxygen and/or moisture present in the hermetically sealed environment 230, and thus reduce the level of oxygen and/or moisture found in the hermetically sealed environment 230. Thus, the oxygen and/or moisture absorbing substance may preserve the integrity of any coatings which may be applied to a portion of the catheter 210, such as a coating applied to the elongate shaft 222 and/or a coating applied to the stent 216, as discussed above. In some embodiments, the oxygen and/or moisture absorbing substance may be selectively activated and/or selectively exposed to the hermetically sealed environment 230 as the plug 330 is inserted into the lumen 18 of the carrier 12 or after the plug 330 has been inserted into the lumen 18 of the carrier tube 12.

As shown in FIG. 8B, when the plug 330 is fully inserted into the carrier tube 12 to establish the hermetically sealed environment 230, the first end 332 of the plug 330 may be located proximate to the distal end of the catheter 210, and thus proximate to the inflation balloon 214 and/or the stent 216. For example, the first end 332 of the plug 330 may be located within about 5 inches, within about 4 inches, within about 3 inches, within about 2 inches, or within about 1 inch of the distal end of the catheter 210. Thus, the oxygen and/or moisture absorbing substance, if present, may be close to the stent 216, for example, to absorb oxygen and/or moisture in the hermetically sealed environment 230 adjacent the stent 216.

It is to be noted that in other embodiments a sterilization fluid, such as ethylene oxide, may be introduced into the lumen 18 of the carrier tube 12 prior to placing the plug 330 into the lumen 18 of the carrier tube 12. In yet other embodiments, the portion of the catheter 210 located within the confines of the carrier tube 12 may be sterilized after the hermetically sealed environment within the carrier tube 12 has been established when the plug 330 has been inserted into the lumen 18 of the carrier tube 12 at the distal end 16 of the carrier tube 12. For example, in such an embodiment, sterilization may be accomplished using gamma radiation or electron beam (E-beam) sterilization.

With the catheter 210 located in a hermetically sealed environment 230 within the carrier tube 12, which may be a sterilized environment, the carrier tube assembly 10 may be packaged in other container or package as desired, without concern as to whether the additional package maintains a sterilized environment. For example, the catheter tube assembly 10 may be packaged in a plastic and/or foil pouch, a tray, or other packaging for distribution, which need not establish a sterilized environment for the catheter 210. Thus, costs associated with providing such a sealed pouch or tray may be avoided with the catheter carrier tube assembly 10 disclosed herein.

Those skilled in the art will recognize that the present invention may be manifested in a variety of forms other than the specific embodiments described and contemplated herein. Accordingly, departure in form and detail may be made without departing from the scope and spirit of the present invention as described in the appended claims.

What is claimed is:

1. A carrier tube assembly for packaging a medical catheter, the carrier tube assembly comprising:
   an elongate tube having a proximal end, a distal end and a lumen extending therethrough;
   a medical catheter including a hub assembly and an elongate shaft extending distally from the hub assembly, at least a distal portion of the elongate shaft of the medical catheter positioned in the lumen of the elongate tube, wherein the proximal end of the elongate tube is hermetically sealed around a portion of the hub assembly of the medical catheter;
   a plug inserted into the lumen of the elongate tube at the distal end of the elongate tube, the plug hermetically sealing the distal end of the elongate tube, the plug includes an annular wall having an interior surface and an exterior surface, wherein the annular wall of the plug includes one or more slots extending through the annular wall from the exterior surface to the interior surface;
   wherein a hermetically sealed environment is established within the elongate tube; and
   wherein the plug includes a moisture and/or oxygen absorbing agent to absorb moisture and/or oxygen in the hermetically sealed environment.

2. The carrier tube assembly of claim 1, wherein the plug is formed of a polymeric material, wherein the moisture and/or oxygen absorbing agent is incorporated into the polymeric material of the plug.

3. The carrier tube assembly of claim 1, wherein the plug includes a bore defining an interior surface, wherein the moisture and/or oxygen absorbing agent is included in a layer of material located on the interior surface of the plug.

4. The carrier tube assembly of claim 1, wherein the plug includes a core of a first material and an outer portion of a second material, wherein the moisture and/or oxygen absorbing agent is included in the core.

5. The carrier tube assembly of claim 4, further including a frangible layer of material separating the core from the hermetically sealed environment.

6. The carrier tube assembly of claim 5, wherein the frangible layer of material is broken to expose the core to the hermetically sealed environment.

7. The carrier tube assembly of claim 1, wherein the plug includes a circumferential exterior surface, wherein the exterior surface includes one or more recesses.

8. The carrier tube assembly of claim 7, wherein the one or more recesses are concave grooves.

9. A carrier tube assembly for packaging a medical catheter, the carrier tube assembly comprising:
   an elongate tube having a proximal end, a distal end and a lumen extending therethrough;
   a medical catheter including a hub assembly and an elongate shaft extending distally from the hub assembly, at least a distal portion of the elongate shaft of the medical catheter positioned in the lumen of the elongate tube, wherein the proximal end of the elongate tube is hermetically sealed around a portion of the hub assembly of the medical catheter;

a plug inserted into the lumen of the elongate tube at the distal end of the elongate tube, the plug hermetically sealing the distal end of the elongate tube, the plug includes an annular wall having an interior surface and an exterior surface, wherein the annular wall of the plug includes one or more slots extending through the annular wall from the exterior surface to the interior surface;

wherein a hermetically sealed environment is established within the elongate tube; and wherein the plug includes a means for reducing the quantity of moisture and/or oxygen within the hermetically sealed environment.

10. The carrier tube assembly of claim 9, wherein the plug includes a moisture and/or oxygen reducing agent.

11. The carrier tube assembly of claim 9, wherein the plug includes an oxidizing agent.

12. The carrier tube assembly of claim 9, wherein the plug includes a desiccant.

13. The carrier tube assembly of claim 12, wherein the plug is formed of a polymeric material, wherein the desiccant is incorporated into the polymeric material of the plug.

14. The carrier tube assembly of claim 12, wherein the plug includes a bore defining an interior surface, wherein the desiccant is included in a layer of material located on the interior surface of the plug.

15. The carrier tube assembly of claim 12, wherein the plug includes a core of a first material and an outer portion of a second material, wherein the desiccant is included in the core.

16. The carrier tube assembly of claim 9, wherein the plug includes an oxygen scavenger.

17. A carrier tube assembly for packaging a medical catheter, the carrier tube assembly comprising:

an elongate tube having a proximal end, a distal end and a lumen extending therethrough;

a medical catheter including a hub assembly and an elongate shaft extending distally from the hub assembly, at least a distal portion of the elongate shaft of the medical catheter positioned in the lumen of the elongate tube, wherein the proximal end of the elongate tube is hermetically sealed around a portion of the hub assembly of the medical catheter; and a cylindrical plug having a first end, a second end, and an exterior surface, the first end of the cylindrical plug inserted into the lumen of the elongate tube at the distal end of the elongate tube such that the exterior surface of the plug is in contact with an inner surface of the elongate tube to hermetically seal the distal end of the elongate tube, the plug including a central bore extending from the first end of the plug toward the second end, wherein the central bore defines an interior surface of the plug;

wherein the plug includes one or more openings extending into the central bore from the exterior surface to the interior surface, and wherein the central bore is in fluid communication with the lumen of the elongate tube.

18. The carrier tube assembly of claim 17, wherein the plug includes a moisture and/or oxygen absorbing material to absorb moisture and/or oxygen sealed within the elongate tube.

19. A method of packaging and sterilizing a medical catheter, the method comprising:

providing a medical catheter having a hub assembly and an elongate shaft extending distally from the hub assembly;

providing an elongate tube having a proximal end, a distal end and a lumen extending from the proximal end to the distal end;

providing a plug having a first end and a the plug includes an annular wall defining a central bore, and wherein the one or more fluid pathways are one or more openings extending through the annular wall to the central bore;

positioning at least a distal portion of the elongate shaft of the medical catheter into the lumen of the elongate tube;

hermetically sealing the proximal end of the elongate tube around a portion of the hub assembly of the medical catheter;

partially inserting the plug into the lumen of the elongate tube at the distal end of the elongate tube to a first position, wherein in the first position the first end of the plug is located within the lumen of the elongate tube proximal of the distal end of the elongate tube a first distance, wherein in the first position one or more fluid pathways are open for introducing a sterilization fluid from exterior of the elongate tube, past the plug and into the lumen of the elongate tube;

with the plug in the first position, introducing a sterilization fluid into the lumen of the elongate tube through the one or more fluid pathways to sterilize the medical catheter; and after the step of introducing a sterilization fluid into the lumen of the elongate tube, further inserting the plug into the lumen of the elongate tube to a second position, wherein in the second position the first end of the plug is located within the lumen of the elongate tube proximal of the distal end of the elongate tube a second distance greater than the first distance, wherein in the second position the distal end of the elongate tube is hermetically sealed with the plug, establishing a hermetically sealed environment within the elongate tube.

20. The method of claim 19, wherein in the second position, the elongate tube covers the one or more fluid pathways.

21. The method of claim 19, wherein the plug includes a circumferential exterior surface, and wherein the one or more fluid pathways are one or more concave flutes formed in the exterior surface.

22. The method of claim 19, wherein the plug includes a moisture and/or oxygen absorbing material.

23. The method of claim 22, wherein the moisture and/or or oxygen absorbing material includes an oxygen scavenger.

24. The method of claim 22, wherein the moisture and/or oxygen absorbing material includes a desiccant.

25. The method of claim 22, further comprising the step of activating the moisture and/or oxygen absorbing material after the step of introducing a sterilization fluid into the lumen of the elongate shaft.

26. The method of claim 22, further comprising the step of exposing the moisture and/or oxygen absorbing material to the hermetically sealed environment after the step of introducing a sterilization fluid into the lumen of the elongate shaft.

* * * * *